(12) United States Patent
Ital et al.

(10) Patent No.: US 8,679,046 B2
(45) Date of Patent: Mar. 25, 2014

(54) SUPPORTING DEVICE

(75) Inventors: Mark Ital, Stuttgart (DE); Thomas Bächle, Sindelfingen (DE); Ismail Bahadir Pamir, Ostfildern (DE); Urs Schneider, Stuttgart (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 292 days.

(21) Appl. No.: 12/826,042

(22) Filed: Jun. 29, 2010

(65) Prior Publication Data
US 2011/0319801 A1 Dec. 29, 2011

(30) Foreign Application Priority Data
Jun. 29, 2010 (DE) .......................... 10 2009 031 195

(51) Int. Cl.
*A61F 5/00* (2006.01)

(52) U.S. Cl.
USPC .................................. 602/23; 602/26; 602/27

(58) Field of Classification Search
USPC ............................ 602/5, 23–27; 128/869, 882
See application file for complete search history.

(56) References Cited

U.S. PATENT DOCUMENTS

| | | | |
|---|---|---|---|
| 1,660,721 A | 7/1928 | Schrag | |
| 4,977,891 A | 12/1990 | Grim | |
| 5,250,021 A * | 10/1993 | Chang | ............................. 602/27 |
| 6,024,713 A | 2/2000 | Barney | |
| 7,507,216 B2 * | 3/2009 | Buckman et al. | ............... 602/32 |
| 7,534,216 B2 | 5/2009 | Jacobs | |
| 7,611,476 B2 * | 11/2009 | Taranow | ......................... 602/16 |
| 2002/0183673 A1 | 12/2002 | Naft et al. | |
| 2003/0109817 A1 * | 6/2003 | Berl | .................................. 602/5 |
| 2006/0211967 A1 | 9/2006 | Reynolds | |
| 2008/0051686 A1 | 2/2008 | Ashihara | |
| 2010/0191347 A1 | 7/2010 | Pusch et al. | |

FOREIGN PATENT DOCUMENTS

| | | |
|---|---|---|
| DE | 9406117 | 9/1994 |
| DE | 69629343 | 10/1996 |
| DE | 69310826 | 10/1997 |
| DE | 10004561 | 2/2000 |
| DE | 20117080 | 1/2002 |
| DE | 202004 004 852 | 6/2004 |
| DE | 10392251 | 3/2005 |
| DE | 60017944 | 5/2006 |
| DE | 102006011465 | 9/2007 |
| DE | 102007032090 | 1/2009 |

(Continued)

OTHER PUBLICATIONS

French Office Action for corresponding patent application No. 1055207 dated Aug. 16, 2012.

*Primary Examiner* — Michael A. Brown
(74) *Attorney, Agent, or Firm* — Renner, Otto, Boisselle & Sklar LLP

(57) ABSTRACT

The invention relates to a supporting device for a support (12) used to support a lower extremity, in particular a knee joint, a lower leg, a foot or an ankle, an upper leg support (14) and a lower leg support (16) being provided and interconnected via an articulation (17), the upper leg support (14) comprises at least a load-bearing surface (24, 28), the lower leg support (16) comprises at least a load-bearing surface (31), a support fixing (18) is provided, which engages with the support (12), the lower leg support (16) and the support fixing (18) being coupled to one another for the transfer of force.

20 Claims, 3 Drawing Sheets

(56) References Cited  * cited by examiner

FOREIGN PATENT DOCUMENTS

| | | |
|---|---|---|
| GB | 790053 | 1/1955 |
| GB | 790053 | 2/1958 |
| WO | 2007/065706 | 6/2007 |
| WO | 2007 065706 | 6/2007 |

SUPPORTING DEVICE

This application claims priority of German Patent Application No. 10 2009 031 195.5 filed Jun. 29, 2010, which is hereby incorporated herein by reference in its entirety.

The invention relates to a supporting device for a support used to support a lower extremity.

Until now, when injuries were sustained to the knee, lower leg, foot or ankle a cast was provided in order to immobilise the lower extremity until a certain point of the healing process had been reached and the cast could therefore be removed. The injured person requires crutches in order to walk. Mobility is therefore restricted. For example daily household activities requiring use of the hands is also considerably restricted since the person has to hold onto the crutches so they can walk.

DE 600 17 944 T2 discloses an orthopaedic device that immobilises the lower extremity. A support of this type poses the advantage that it can be fitted and removed quickly and easily, in such a way that the drawbacks encountered with a cast, which is in place for a long time, are eradicated. With many types of injury to the lower extremity however, in particular in the case of breaks, it is necessary to avoid any loading at the point of break during the primary healing phase. Crutches must therefore also be used with these orthopaedic devices. These crutches are not necessary in the case of injuries to the soft tissue of the lower extremities since the supports also make it possible to walk without the use of crutches. In the case of a broken bone or the like the injured person therefore remains restricted with regard to use of their hands, at least during the primary healing phase, owing to the use of crutches. Controlled loading for controlled rehabilitation is also not provided by these supports.

DE 10 2006 011 465 A1 discloses a knee brace, in which an upper leg support and a lower leg support are connected to one another via an articulation. This supporting device is fixed to the upper leg and to the lower leg by fixing straps. Projections are provided at the lower end of the lower leg support, which are adapted to and also support the tibia condyle. It is thus possible to relieve any loading of the knee.

US 2003/0109817 A1 discloses a knee brace, in which the force is passed into the supporting device via the upper leg support and transferred directly to the ground via the knee articulation and the lower leg support so as to relieve any loading of the knee. The lower leg support comprises a cushioning means between an upper and lower support rod.

US 2006/0211967 A1 also discloses a knee brace that comprises an upper leg support and a lower leg support. A movement mechanism is controlled between a calf and foot shell and the lower leg support so as to control or lock the foot shell during a stepping movement. In order to use the knee braces according to DE 10 2006 011 465 A1, US 2003/0109817 and US 2006/0211967 there must be no injuries to the lower extremities so these knee braces can be applied and relieve the knee of any loading.

The object of the invention is to propose a supporting device that, in particular in the event of an injury to the lower extremities, makes it possible for the patient to walk without the use of crutches, even during the primary healing phase. In particular controlled rehabilitation is made possible, during which overloading is preferably prevented.

This object is achieved in accordance with the invention by the features of claim 1. Further advantageous embodiments and developments are disclosed in other dependent claims.

The supporting device according to the invention comprises an upper leg support and a lower leg support that are interconnected via an articulation, the upper leg support comprising at least a load-bearing surface that abuts the pelvis and/or upper leg. The supporting device further comprises a lower leg support having a support fixing for a support, a cushioning means being provided between the lower leg support and the support fixing, which are coupled to one another for the transfer of any force and the cushioning force of which is adjustable.

Instead of the previous transfer of force via the crutches in order to relieve loading of the injured leg this supporting device now therefore makes it possible for force to be transferred via the supporting device and the support at the injured leg, the supporting device in conjunction with the support causing the force exerted when walking to pass into the supporting device owing to the weight of the human body and to be transferred from the supporting device to the ground via the support. It is thus possible to walk without crutches, i.e. the hands are kept free, for example so as to carry objects from one place to another. Owing to the use of the supporting device the injured person is therefore mobile right from the start, i.e. during the primary healing phase, once a support has been fitted to the lower extremity. The cushioning means also makes it possible to achieve controlled rehabilitation. Directly after the primary healing phase it is generally desirable for the lower extremity to initially be loaded, for example with 10% or 20% of the maximum loading capacity so as to counteract any muscle wastage and the risk of oedema. It is generally impossible for a person to carry out this task. By adjusting the cushioning force of the cushioning means it is possible to adjust the desired loading capacity in such a way that, during walking, a cushioning movement is produced between the support fixing and the lower leg support that allows, for example, 10% or 20% loading.

A further preferred configuration of the supporting device provides for the cushioning means or the boot arrangement to comprise a pressure or load detection means, in particular a pressure sensor. The desired load can be measured by a pressure or load detection means of this type and a cushioning effect of the cushioning means can therefore be adjusted. For example a pressure sensor may be integrated into the cushioning means or else be provided in such a way that the boot arrangement comprises a sole plate configured, for example, as a pressure-measuring sole, or one or more pressure sensors are distributed in the sole plate so the loading body weight can be measured. Loading can thus be increased selectively at predetermined or desired intervals.

Furthermore it is preferably provided for the pressure or load detection means to comprise a pressure-measuring sole, which detects the pressure or force acting thereon capacitively, inductively or by way of piezo effect. The data detected is preferably transferred wirelessly from the pressure sensors to an evaluation means that can be fixed to the supporting device or integrated into individual regions in the supporting device. Wireless or wired transfer can then be effected from there to an external evaluation means. Wired data transfer may also be made possible between the pressure sensor and the evaluation means that is provided at the supporting device.

The cushioning means can preferably be adjusted to a cushioning path of zero, in such a way that a rigid connection is provided between the lower leg support and the support fixing. This adjustment mode is selected, in particular during the primary healing phase, so no load is exerted on the lower extremity and, instead, any force exerted is transferred completely from the support fixing to the lower leg support when full loading is desired.

In accordance with a further preferred configuration of the invention the cushioning path can be adjusted as a function of the loading capacity that is optimal for the healing process. This cushioning means therefore makes it possible for a predetermined cushioning path to be released and, once this cushioning path has been passed through, for the support fixing to be held at a defined distance from the lower leg support, i.e. for any further loading to no longer be exerted on the lower extremity, but to be absorbed by the supporting device and the support. Overloading can therefore be avoided and controlled rehabilitation can be optimised for quicker mobilisation. At the same time, the load may be monitored or compared with the values detected by the load detection means.

In accordance with a further preferred configuration of the cushioning means the cushioning means comprises at least a mechanical cushioning member, in particular a tension or compression spring, a pneumatic, hydraulic, electromagnetic cushioning member or a resilient energy-storing member. The appropriate cushioning members may be provided as a function of the field of application and the space available for fitting. A simple embodiment is provided by the formation of a tension or compression spring. In this case coil springs may be used. Alternatively stacked, cupped spring washers may also be used. The spring constant and the spring characteristics of cushioning members of this type can be adapted precisely to different loading requirements. Furthermore, a pneumatic cushioning member, for example an air cushion, or a hydraulic cushioning member, for example as a hydraulic piston, may be provided. Electromagnetic cushioning members may also be arranged, in which a coil is movable relative to an iron core. Resilient energy-storing members, rubber-like or resiliently deformable cushioning members or else cushioning members made of foam or the like may also be provided.

Furthermore, one or more, preferably two mutually opposed guides are preferably arranged between the lower leg support and the support fixing. The relative movement between the support fixing and the lower leg fixing can therefore be guided. The guide/guides is/are preferably associated directly with the articulation in such a way that an optimal flow of force is made possible from the upper leg support to the lower leg support and the support fixing via the knee articulation.

In accordance with a further preferred configuration of the invention the support fixing is fixed to the upper end or upper edge region of the support and each guide is arranged beside the articulation. A very compact configuration of the supporting device can thus be made possible. In addition the support fixing may also be supported at the upper edge of the support. The support may preferably comprise one or more engagement points, for example projections or a shoulder, to provide support when the support fixing engages with the upper edge region of the support.

Furthermore the lower leg support preferably comprises a load-bearing surface, which abuts the lower knee or knee bone of the lower leg. This load-bearing surface is preferably configured so as to be saucer-shaped. Owing to the hump-like configuration at the lower leg a particularly good load-bearing capacity can be achieved and force can be passed effectively into the supporting device. This capacity is approximately 30% to 50% of the entire load-bearing capacity of the supporting device.

A cushioning member is preferably provided beneath the load-bearing surface of the lower leg support and is supported oppositely at the support fixing. A direct transfer of force can thus be made possible. At the same time a free space is thus created in the region of the hollow of the knee, in such a way that the supporting device does not restrict freedom of movement in any way.

In accordance with an alternative configuration of the supporting device it is provided for the support fixing to be fixed to the support in the region of the ankle joint and to comprise lateral guide portions, which are guided movably to and fro at guides, the guides each being associated with the articulation between the upper and lower leg supports and each being rigidly arranged at the lower leg support as well as extending along the support and comprising a sole plate at the lower end, which sole plate rolls over the ground. This alternative embodiment is advantageous, in particular if the outer shell of the support is configured so as to be not completely loadable. Force does not flow via the support through the lateral guides, which are provided between the sole plate and the load-bearing surface of the lower leg support, but instead may flow exclusively via the supporting device. The support is, however, guided movably relative to the supporting device via the guide portions of the support fixing.

Furthermore, in this alternative embodiment the cushioning means is preferably provided between the sole plate and the guide portion of the support fixing. Controlled rehabilitation can therefore be provided in turn.

Furthermore, in this alternative embodiment a fixing portion engaging with the upper region of the support is preferably arranged beneath the load-bearing surface of the lower leg. This fixing portion stabilises the support relative to the lower leg support so the support is only movable to and fro and movement in other directions is prevented.

A preferred configuration provides for the support to be arranged detachably relative to the support fixing. This detachable arrangement of the support is advantageous, in particular in the configuration of the supporting device with lateral guide portions at guides that extend from the articulation to the sole plate. The lower leg can thus be bent relative to the upper leg and, if the articulation is locked, force is transferred directly from the upper leg support to the lower leg support, via the articulation, and to the ground via the sole plate. With this arrangement or loading instance no force whatsoever is exerted on the foot. This arrangement also poses the advantage that with a supporting device of this type, if the articulation is locked in order to prevent any pivoting movement of the lower leg relative to the upper leg then there is no need to adapt the sole thickness to the healthy foot since the height of the supporting device, owing to the bent foot, only has to be geared to the height of the healthy foot. If compensation of this type were not provided, then the pelvis would be slanted, which would prevent a normal walking movement and could lead to discomfort. In this case the support fixing may, for example, be configured as a hook-and-loop fastening belt or other belt configured with an adjustable and detachable fastening so as to enable both a rigid arrangement relative to the lower leg support and a detachable arrangement.

A further preferred configuration of the invention provides for the support fixing to engage with the support via a fixing strap, a screwed connection, a clamped connection, a locking connection or an adhesive connection or lamination. A fixing strap comprising a hook-and-loop fastening or a belt fastening is preferably provided, whereby the supporting device can be fixed to the support and replaced quickly and easily.

In accordance with a further preferred configuration of the invention the upper leg support comprises a load-bearing surface that abuts the ischium, pubis or pelvis and preferably comprises a pressure-distributing or pressure-minimising pad. The upper leg support additionally comprises a fixing strap, which surrounds the upper leg. A fixing strap of this type makes it possible to fix the upper leg support to the upper leg over a large surface area, whereby loading can be sustained and force can be transferred.

In accordance with a further preferred configuration of the upper leg support a preferably hook-shaped curve is provided at the upper end of said support, a supporting pad being arranged on the upper face of this curve and abutting an ischium hump, ischium, pubis or the pelvis to provide support. A particularly large amount of force can therefore pass through. For example a seat cushion, similar to a saddle, is provided and is arranged so as to absorb force via the pelvis. This cushion is preferably made of plastics materials, such as thermosets, thermoplastics and/or elastomers. Bonded fabrics, composite foams, natural material, silicone, gels and/or a combination of these materials may also be used so pressure points can be selectively cushioned and the user's comfort during wear is therefore improved.

In accordance with a further preferred configuration of the invention the lower leg support comprises a fixing strap. The load-bearing surface can thus be fixed to the lower knee.

The invention and further advantageous embodiments and developments thereof will be described and explained in greater detail hereinafter with reference to the examples illustrated in the drawings. The features inferred from the description and the drawings may be applied in accordance with the invention either individually or together in any combination. In the drawings.

Figure 1:
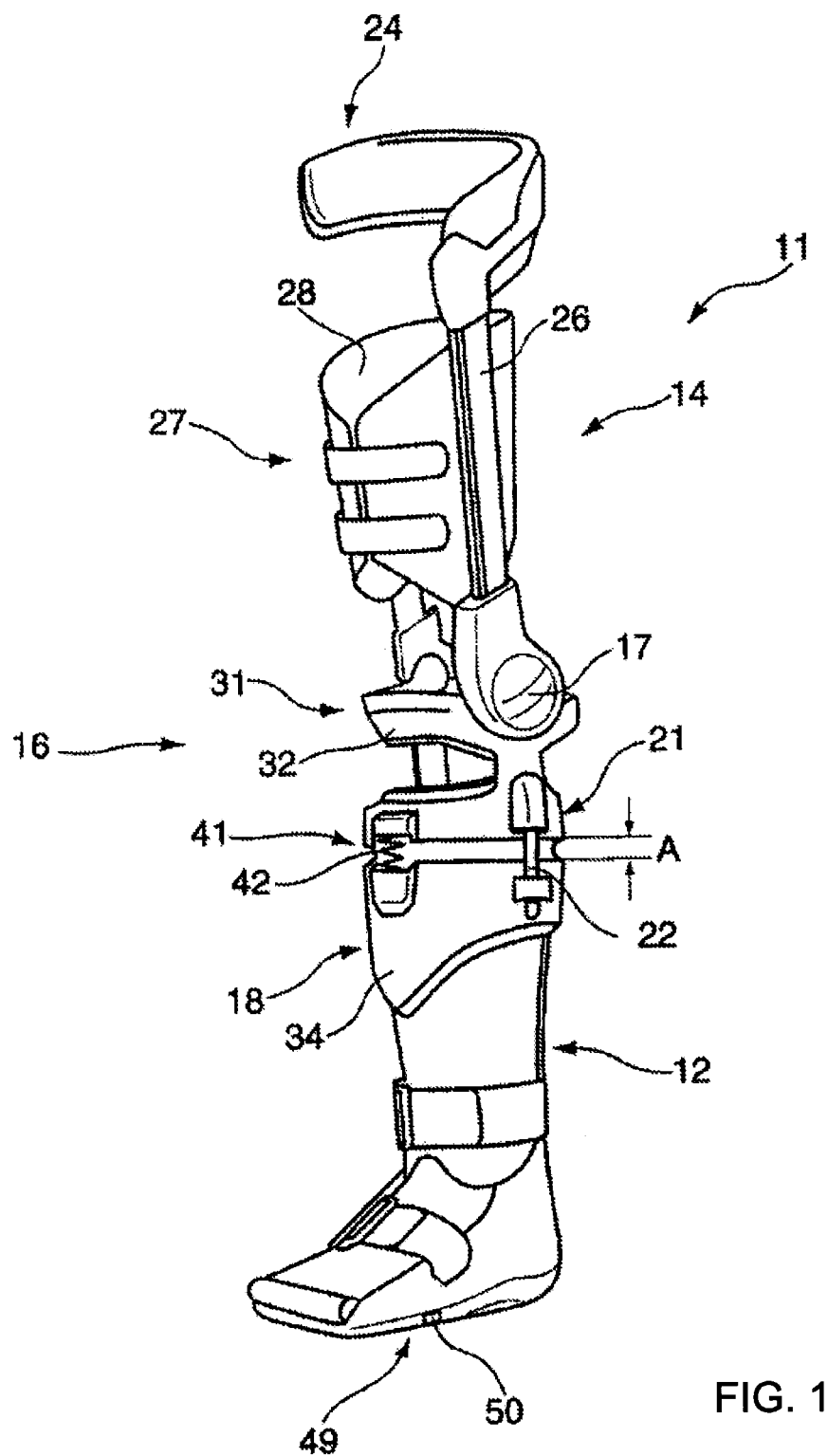
FIG. 1 is a schematic view of a first embodiment of a supporting device.

With reference to FIG. 1 a schematic view from the front of a supporting device 11 is illustrated, which device is attached to a support 12. A support 12 of this type may, for example, be available from Aircast Inc., Summit, N.J., US and, for example, is disclosed in greater detail in DE 600 17 944 T2. The support 12 is preferably configured as an orthopaedic ankle joint support. This comprises a boot arrangement that can sustain the load exerted by walking and is formed of one or more shell members, these shell members preferably being made of deflection-resistant or pressure-resistant plastics materials. The shell members may comprise air cushions and/or gel cushions at the inner face facing the foot. For example a boot may be provided that is configured as a shell member, only the tongue of the boot consisting of a flexible material so it can be put on and removed more easily. The boot may be fastened using hook-and-loop strips, straps or the like. Other boot arrangements may also be used.

The boot arrangement that can preferably sustain the load exerted by walking and is configured as the support 12 may preferably comprise a pressure or load detection means 49, which comprises at least a pressure sensor 50 that is arranged, for example, on the insole of the support 12 or beneath a thin protective layer so as to form a type of pressure-measuring sole and so as to protect the pressure-measuring sole against damage. The load exerted on the leg can thus be detected. The detected data are supplied to an evaluation unit via a cable or wirelessly, said evaluation unit being fixed to the supporting device 11 or even integrated. This evaluation unit, which preferably comprises at least an IC module with a memory, can in turn transfer the detected and evaluated data to an external evaluation means, in particular a computer, wirelessly or else via a connection socket, for example a USB connection, fire wire or a similar connection or the like. A display may also be provided at the supporting device 11, which displays the load, for example as a percentage or in kilograms, in such a way that the user knows the current load, the load that is required and whether this is too high or too low so as to therefore be able to preferably set the corresponding required or desired load himself. This setting may also be secured in such a way that only an authorised individual, in particular the doctor, can make changes of this type to the setting.

The supporting device 11 comprises an upper leg support 14 and a lower leg support 16, which are interconnected via an articulation, in particular a double articulation 17. The lower leg support 16 is motionally coupled to a support fixing 18. In the embodiment according to FIG. 1 the support fixing 18 is guided via a guide 21 relative to the lower leg support 16 in a non-rotational manner, movably to and fro. One or more guide rods 22 may therefore be arranged so as to guide the support portion 18 relative the lower leg support 16. One or two mutually parallel guide rods 22 is/are associated with the articulation 17 in each case.

In a first embodiment it may be provided for a defined distance to be set between the lower leg support 16 and the support portion 18 via the guide rods 22, which are preferably replaceable. The supporting device 11 can therefore be used as early as a primary healing phase since the lower extremity is not loaded. Crutches are not necessary.

The upper leg support 14 comprises a load-bearing surface 24, which in this embodiment is formed by a hook-shaped curve of a supporting strut 26. The load-bearing surface 24 preferably comprises a seat cushion and is configured similarly to a saddle in such a way that this load-bearing surface 24 abuts the pelvis or an ischium hump. The supporting strut 26 is connected to the right and left articulation 17 in such a way that it is possible to transfer force. This articulation may also be set so as to be completely rigid in order to ensure that the leg is completely relieved of loading. In order to make it possible to sit comfortably, if an angle setting defined by the doctor is approved during further progression of treatment, a corresponding angular deflection may be set and freedom of movement can therefore be determined and limited. The supporting strut 26 may also comprise a fixing strap 27, for example having hook-and-loop fasteners, in such a way that an additional load-bearing surface 28 is created once the fixing strap 27 has been applied to the upper leg.

A load-bearing surface 31 is arranged at the lower leg support 16 and abuts the lower knee. This load-bearing surface 31 is provided in a semi-circular knee strap 32, which is held in place by a guide rod 22 in each case and, in particular, is associated with the articulation 17. The knee strap 32 may be configured as a resilient strap and may be individually adjustable in length so it is possible to achieve an optimal fit of the lower leg support 16 and to transfer force. Alternatively the knee strap 32 may also be saucer-shaped and preferably comprises gel cushions and/or air cushions at its inner face to hold and fit the knee closely. In particular it may be provided for the filling volume of the air cushions to be individually adjustable. Alternatively it may also be provided for the load-bearing surface 31 to directly engage with or be connected to the articulation 17. A fixing strap 27 may also be configured at the lower leg support 16 in order to position the load-bearing surface 31 so it rests rigidly against the lower knee.

The support fixing 18 is preferably fixed to the support 12 by a fixing strap 34. This fixing strap 34 may, for example, consist of two half shells, which are placed on an upper edge of the support 12 or surround an upper edge region and are held in place by a clamped connection. If a clamped connection is provided at the edge region then the at least one shell member of the support 12 may preferably comprise a peripheral shoulder or projection so as to make it possible for the fixing strap 34 to engage positively with the at least one shell member of the support 12. Alternatively a plug-in and/or screwed connection may also be provided. In this alternative embodiment it is provided for the support 12 to comprise suitably configured members, which are attached to the at least one shell member of the support 12 or are integrated during production of the at least one shell member, or can be attached or fixed subsequently so as to form part of the screwed and/or plug-in connection. Furthermore the support 12 and the support fixing 18 may comprise fixing members that are coordinated with one another in such a way that a lock-snap connection or a releasable plug-in connection or the like is provided. Furthermore the support fixing 18 may alternatively be fixed to the support 12 by way of adhesion or lamination.

In accordance with this preferred embodiment the supporting device 11 therefore comprises the load-bearing surfaces 24 and 28 at the upper leg support 14 and the load-bearing surface 31 at the lower leg support 16. A particular level of comfort during wear is therefore provided. Alternatively the supporting device 11 may only comprise the load-bearing surface 24 or only the load-bearing surface 28 at the upper leg support 14. However, at least one of the two load-bearing surfaces 24 and 28 may preferably be provided at the upper leg support 14 or at least one load-bearing surface 31 may preferably be provided at the lower leg support 16.

Alternatively to the rigid arrangement between the support fixing 18 and the lower leg support 16, a cushioning means 41 may be positioned between the lower leg support 16 and the support fixing 18. This cushioning means 41 is preferably adjustable, i.e. it is possible to set a fixed distance between the lower leg support and the support fixing 18 using this cushioning means 41. The permanently adjustable distance can be adapted in length to the respective circumstance. The cushioning means also makes it possible to set a defined cushioning path. This setting is made by adaptation to the healing progress and the increasing loading capacity of the lower extremity. As soon as the defined cushioning path has been exceeded owing to excess load, the cushioning means 41 adopts a blocking action or a predetermined fixed distance between the support fixing 18 and the lower leg fixing 16 is occupied. Overloading is thus prevented. In order to adjust a predetermined cushioning path A, a stop that is movable to and fro may be set to a predetermined distance, for example via an adjustment dial, thus preventing any further movement of the support fixing 18 and the lower leg support 16 relative to one another.

This cushioning means 41 therefore enables use as early as the primary healing phase, the support fixing 18 being set at a fixed distance relative to the lower leg support 16, in such a way that there is no loading of the lower extremity and instead the load is transferred from the supporting device 11 to the ground via the support 12. It is then possible to achieve controlled rehabilitation, in which a cushioning path is released in accordance with the respective load that is optimal for the healing process and is reduced with regard to the maximum load.

The cushioning means 41 comprises at least a cushioning member 42, preferably a compression spring, which is replaceable in particular and is preferably adapted to the body weight of the user so as to preferably provide smooth occupation of a defined cushioning path. Other energy-storing members may be used as an alternatively to the compression spring, in particular rubber-resilient energy-storing members or energy-storing members made of foam. Furthermore different compression springs having an appropriate spring constant may also be used as an alternative to the cushioning path that is adjustable by way of a stop.

The cushioning means 41 is, for example, configured as a pressure loadable cushioning means 41. Alternatively the cushioning means 41 may, of course, also be tensioned. Force passing into the support fixing 18 and the lower leg support 16 is correspondingly deflected.

The cushioning means 41 may be arranged both in the region of the shin and oppositely or laterally directly beside the articulation 17. A suitable arrangement may be provided as a function of the constructional configuration of the guide rod 22 or guide rods 22 and the configuration of the cushioning member 42.

Figure 2:
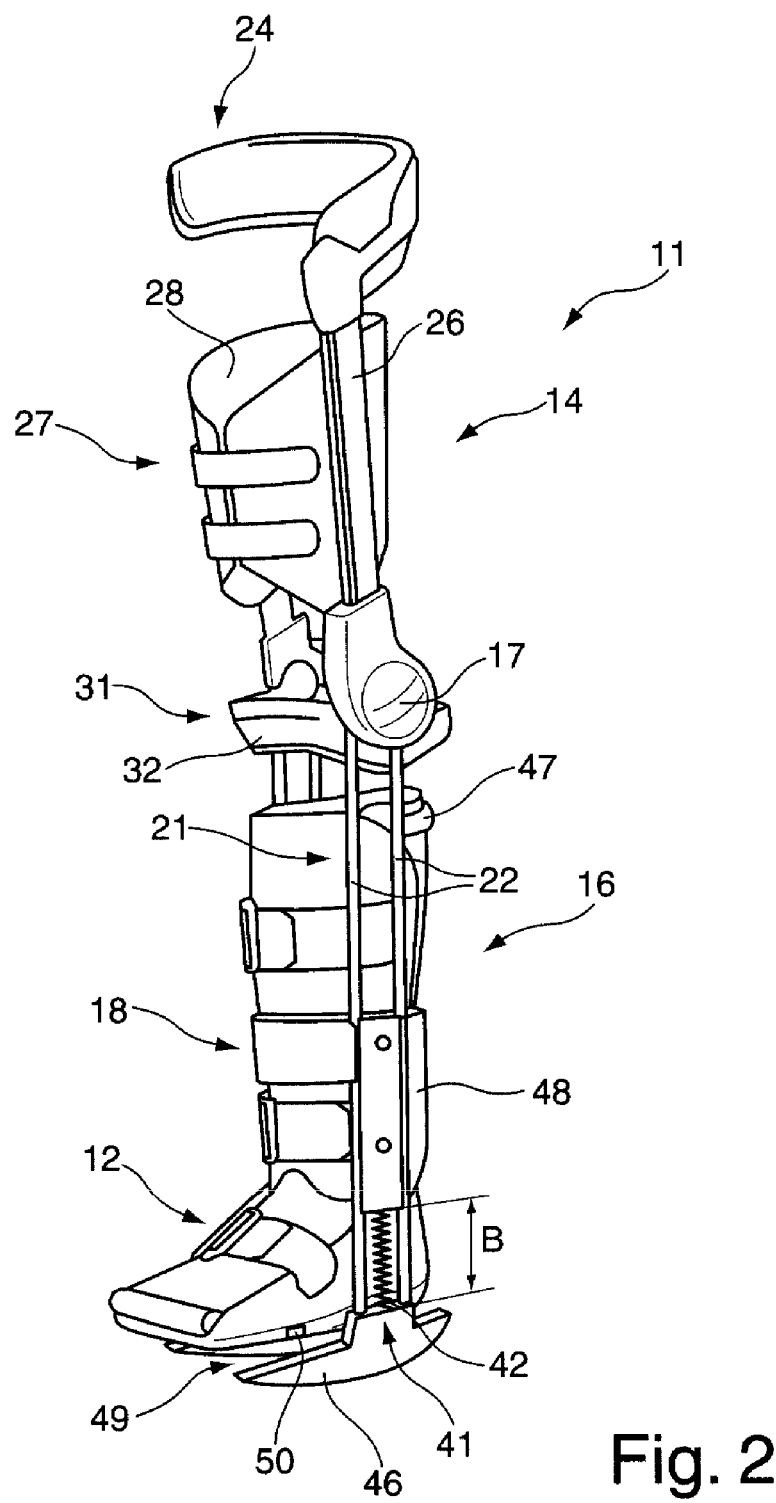
FIG. 2 is a perspective view of an alternative embodiment to FIG. 1.

With reference to FIG. 2 an alternative configuration of a supporting device 11 with regard to that of FIG. 1 is illustrated. The upper leg support 14 has the same function, but a supporting shell 44 is provided instead of a supporting strut 26.

The structure of the lower leg support 16 and of the support fixing 18 differ from those in FIG. 1. In this case guide rods 22 arranged laterally in the direction of action of force relative to the articulation 17 are provided and comprise a sole plate 46 at the lower end. The support fixing 18 is fixed to the support 12 in the region of the ankle joint and comprises a guide portion 48, which is guided between the two guide rods 22 in such a way that the support 12 is movable to and fro relative to the guide 21. The cushioning means 41 is provided between the guide portion 48 and the sole plate 46. A cushioning path B may be adjusted as a function of the set loading capacity. This determines the extent to which the guide rods 22 plunge into the sole plate 46. The cushioning means 41 may also be set to a cushioning path of zero so no load is exerted on the lower extremity. The cushioning means 41 can also be used in this alternative configuration of the supporting device 11 and operates under tension.

In this embodiment a fixing portion 47 is also provided. This fixing portion 47 can only extend around the calf region. The direction of movement for cushioning may only be set along the guide 21 owing to the support provided by the fixing portion 47. The fixing portion 47 may also comprise a strap, which is placed around the shin in such a way that an additional guiding of the support 12 relative to the guide 21 is provided.

Figure 3:
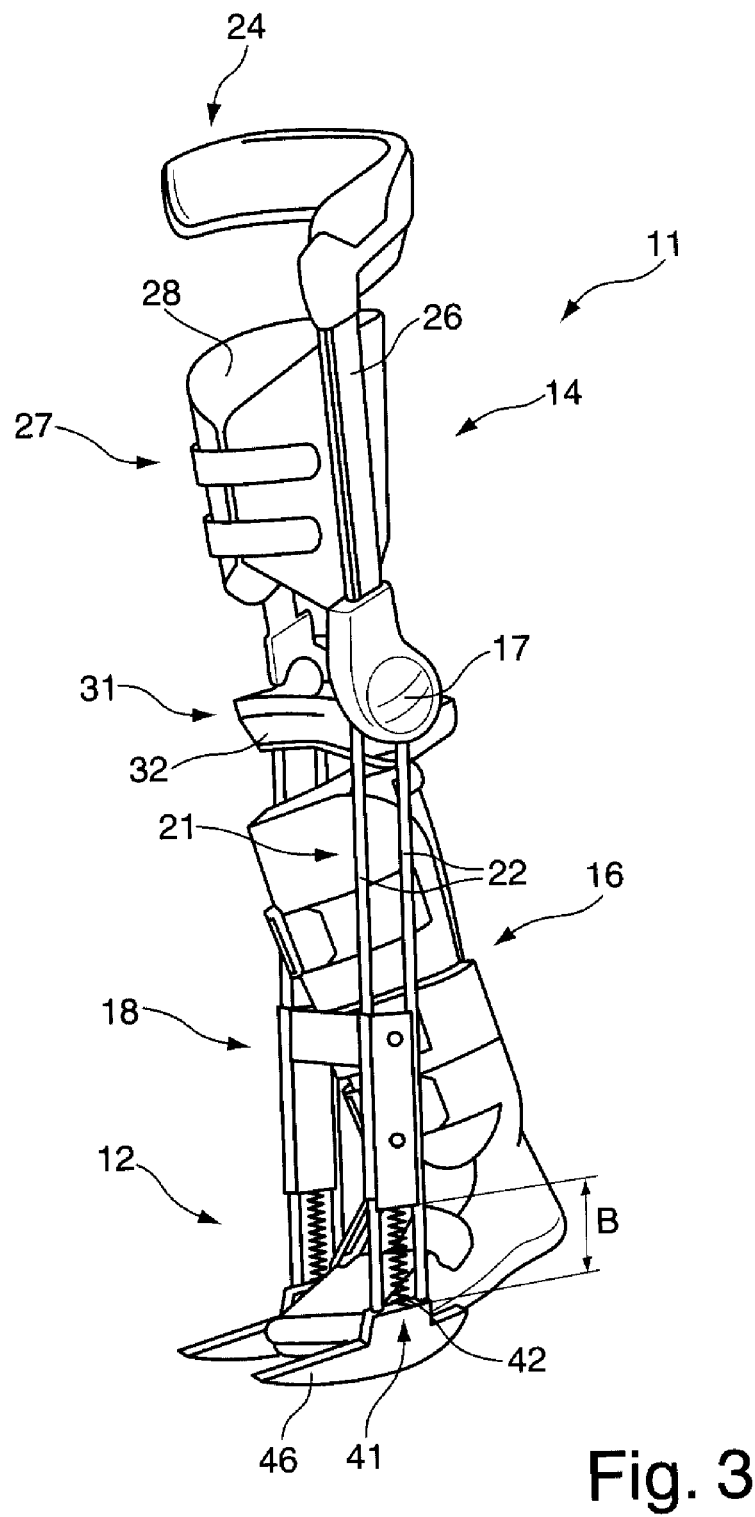
FIG. 3 is a perspective view of an alternative application in accordance with the embodiment according to FIG. 2.

With reference to FIG. 3 an alternative use of the supporting device 11 compared to FIG. 2 is illustrated. In this case it is provided for the support fixing 18 to be provided as a detachable support fixing in such a way that the support 12 can be pivoted out of the position shown in FIG. 2 so as to transfer into a position according to FIG. 3. At the same time the articulation 17 is locked in such a way that the supporting strut 26 and the guide rods 22 make it possible to remove any loading of the sole plate 46. The user's body is therefore supported on the load-bearing surface 46. The user can bend his lower leg relative to the upper leg and relieve it of any loading as well as stand without crutches. Both the lower leg and the knee are therefore completely relieved of loading. In this embodiment the cushioning means 41 is set to a block setting, this means that no cushioning is set or else only such a low level of cushioning is set that this provides comfort during walking, yet the plunging path is very short so the toes don't contact the ground during walking.

The invention claimed is:

1. Supporting device comprising
 a support boot used to support a lower extremity of a person, the support boot including an orthopaedic ankle joint support, an upper leg support and a lower leg support interconnected via an articulation, the upper leg support comprising at least a load bearing surface, the lower leg support including a load-bearing surface for abutting the lower knee when worn by the person, a support fixing for the support boot that can be loaded with the force exerted, and a cushioning member provided between the support fixing and the lower leg support, which are coupled to one another for the transfer of force, and a cushioning force of the cushioning member is adjustable.

2. Supporting device according to claim 1, wherein the cushioning member or the support boot includes a pressure or load detector.

3. Supporting device according to claim 2, wherein the pressure or load detector is a pressure sensor, and the pressure sensor detects a force or a pressure capacitively, inductively or by way of piezo effect.

4. Supporting device according to claim 2, wherein the pressure or load detector is configured as a pressure-measuring sole comprising at least a pressure sensor.

5. Supporting device according to claim 1, wherein the cushioning movement of the cushioning member can be set to zero to provide a rigid connection between the lower leg support and the support fixing.

6. Supporting device according to claim 1, wherein the cushioning movement of the cushioning member is adjustable as a function of the load that is optimal for the healing process in order to achieve controlled rehabilitation.

7. Supporting device according to claim 1, wherein the cushioning member comprises at least a mechanical cushioning member or a pneumatic, hydraulic or electro-magnetic cushioning member or a resilient energy-storing member.

8. Supporting device according to claim 1, wherein relative movement of the lower leg support and the support fixing is guided by one or more, or two mutually opposed guides.

9. Supporting device according to claim 8, wherein the support fixing is fixed to the upper end or upper edge region of the support boot and the guides are each provided beside the articulation or in the articulation.

10. Supporting device according to claim 1, wherein the load bearing surface is saucer-shaped.

11. Supporting device according to claim 1, wherein the cushioning member is provided beneath the load-bearing surface of the lower leg support and is supported oppositely at the support fixing.

12. Supporting device according to claim 1, wherein the support fixing is fixable to the support boot by a fixing strap, a screwed connection, a clamped connection, a locking connection or by an adhesive connection or lamination.

13. Supporting device according to claim 1, wherein the upper leg support comprises a load-bearing surface that abuts the ischium, pubis or pelvis and surrounds the upper leg.

14. Supporting device according to claim 1, wherein the upper leg support comprises at an upper end a supporting strut including a hook-shaped curve at the upper end, a load-bearing surface, being arranged on the upper face of said curve and being provided so as to provide support at the pelvis or ischemic hump.

15. Supporting device according to claim 14, wherein the load-bearing surface is comprising a pressure-distributing or pressure-minimising pad that consists of at least one of a thermoset, thermoplastic and elastomeric material, bonded fabrics, composite foam, natural material or silicone or of a gel mass.

16. Supporting device according to claim 1, wherein the support boot includes at least a shell member that can sustain the load exerted during walking and at least comprises an air cushion and/or gel cushion.

17. Supporting device according to claim 1, wherein the support fixing is fixed to the support boot in the region of the ankle joint and comprises lateral guide portions, which are guided movably to and fro at guides, the guides each being associated with the articulation and being rigidly arranged at the lower leg support as well as comprising a sole plate at the lower end, which sole plate is provided so as to roll over the ground.

18. Supporting device according to claim 17, wherein the cushioning means is positioned between the sole plate and the guide portion of the support fixing.

19. Supporting device according to claim 17, wherein a fixing portion engaging with the upper region of the support is provided beneath the load-bearing surface of the lower leg support.

20. Supporting device according to claim 17, wherein the support boot is arranged detachably relative to the support fixing.

* * * * *